(12) United States Patent
Leroux

(10) Patent No.: US 8,281,648 B2
(45) Date of Patent: Oct. 9, 2012

(54) MATERIAL TESTING APPARATUS WITH NON-CONTACT SENSOR

(75) Inventor: Pierre Leroux, Rancho Santa Margarita, CA (US)

(73) Assignee: Nanovea, Inc., Irvine, CA (US)

( * ) Notice: Subject to any disclaimer, the term of this patent is extended or adjusted under 35 U.S.C. 154(b) by 652 days.

(21) Appl. No.: 12/337,318

(22) Filed: Dec. 17, 2008

(65) Prior Publication Data

US 2009/0158826 A1 Jun. 25, 2009

Related U.S. Application Data

(60) Provisional application No. 61/015,571, filed on Dec. 20, 2007.

(51) Int. Cl.
*G01N 3/48* (2006.01)
*G01N 3/42* (2006.01)

(52) U.S. Cl. .................................. 73/81; 73/82

(58) Field of Classification Search .................. 73/81, 82
See application file for complete search history.

(56) References Cited

U.S. PATENT DOCUMENTS

| | | | |
|---|---|---|---|
| 5,062,293 A | 11/1991 | Bakirov et al. | |
| 5,866,807 A | 2/1999 | Elings et al. | |
| 5,965,896 A | 10/1999 | Marton | |
| 6,134,954 A * | 10/2000 | Suresh et al. | 73/81 |
| 6,301,956 B1 * | 10/2001 | Fujita et al. | 73/82 |
| 6,718,820 B2 * | 4/2004 | Kwon et al. | 73/81 |
| 6,778,916 B2 * | 8/2004 | Lee | 702/42 |
| 6,799,472 B2 * | 10/2004 | Nakayama et al. | 73/827 |
| 6,851,300 B2 * | 2/2005 | Kwon et al. | 73/85 |
| 6,945,097 B2 * | 9/2005 | Jardret et al. | 73/81 |
| 6,978,664 B1 * | 12/2005 | Uchic et al. | 73/85 |
| 7,424,822 B2 * | 9/2008 | Isomoto | 73/81 |
| 7,784,357 B2 * | 8/2010 | Park | 73/859 |
| 2002/0170360 A1 * | 11/2002 | Anand et al. | 73/849 |
| 2007/0151340 A1 * | 7/2007 | Hsu et al. | 73/573 |
| 2007/0157710 A1 | 7/2007 | Isomoto | |
| 2007/0227236 A1 | 10/2007 | Bonilla et al. | |
| 2008/0282783 A1 * | 11/2008 | Valleggi et al. | 73/82 |
| 2009/0145196 A1 * | 6/2009 | Kawazoe et al. | 73/1.89 |

OTHER PUBLICATIONS

International Search Report; Mar. 19, 2009, 2 pages.
Brochure, OMRON Z4M-N30V "Regular Reflective Displacement Sensor", downloaded on Jul. 27, 2011 from http://www.omron247.com/marcom/pdfcatal.nsf/PDFLookupByUniqueID/94357672EBE23A9D86256A31006C1830/$File/D02Z4MN30V0401.pdf?OpenElement.

* cited by examiner

*Primary Examiner* — Lisa Caputo
*Assistant Examiner* — Jamel Williams
(74) *Attorney, Agent, or Firm* — Knobbe Martens Olson & Bear LLP

(57) ABSTRACT

A non-contact sensor is attached to the indenting module with its working range encompassing the tip of the indenter. The sensor directly measures penetration depth of the indenter during scratch, wear or instrumented hardness testing. During the test, the non-contact sensor records the height of the surface as the indenter penetrates the surface of the testing specimen.

20 Claims, 3 Drawing Sheets

MATERIAL TESTING APPARATUS WITH NON-CONTACT SENSOR

CROSS-REFERENCE TO RELATED APPLICATIONS

This application claims the priority benefit of U.S. Provisional Patent Application No. 61/015,571, filed on Dec. 20, 2007, which is hereby incorporated by reference in its entirety.

BACKGROUND OF THE INVENTION

1. Field of the Invention

The present invention generally relates to methods and systems used to measure mechanical properties of materials. More particularly, the present invention relates to such methods and systems in which a penetration depth of an indenter is registered by a non-contact sensor configuration.

2. Description of the Related Art

It is well known that compliance affects the accuracy of depth measurements during hardness, scratch and/or wear testing. Compliance is generally used to describe displacement caused by deformation of parts of the instrument under load, and includes movement of the sample holder caused by loading during testing.

For instrumented indentation hardness testing of a sample, some have used a mechanical arm to touch a sample surface in order to generate a reference location for distance measurement. As the mechanical arm presses against a sample, the reference feeds back the height of the surface.

Because the reference is in mechanical contact with the surface, the accuracy of the data suffers. Also, the geometry of the contact point and the surface roughness of the sample can affect the accuracy of the test results. At the nanometric level, a surface roughness in the micron range will affect the accuracy of the final depth measured even if the claimed resolution of the sensor used (often a capacitor or linear variable differential transformer, or LVDT) is excellent.

Moreover, due to the mechanical contact between the mechanical arm and the sample surface, softer materials, such as plastics or polymers, for instance, cannot be accurately measured because the contact point sinks into the material or because material creep translates into movement of the reference as it deforms the sample being tested.

For scratch and wear testing, it is simply not possible to touch the surface with the same reference while the sample is moving. Therefore, the total plastic and elastic deformation depth during the scratch and wear testing is masked by the effects of compliance.

Because physical contact is limiting and cumbersome, testing samples of varying geometry can be difficult. The mechanical contact also takes more time because it needs to stabilize before testing can start.

SUMMARY OF THE INVENTION

One or more of these and other problems can be solved by using a non-contact sensor to more accurately measure the height of the sample surface during testing. The sensor can be attached to the indenter assembly and, therefore, the depth measured corresponds directly to the penetration depth of the indenter.

The non-contact assembly can comprise a non-contact sensor and a mechanism to adjust the range of the sensor as a function of its height above the surface. This assembly can be attached to the indenter side of the load sensing assembly, for example.

The assembly used in the wear, hardness, or scratch tester can be lowered toward the sample surface. As contact is made with the sample surface, the load cell indicates contact by an increase in the load being measured. The non-contact sensor can be previously adjusted to be within a functioning range or can be adjusted following initial contact of the indenter with the sample surface. During the test, the indenter comes into contact with the surface, which contact is detected by the load cell, and the non-contact depth sensor records the starting position. As the scratch, hardness or wear test is performed, depth data can be continuously recorded with a direct reference to the position of the indenter to the surface of the sample being tested.

One embodiment that is arranged and configured in accordance with certain features, aspects and advantages of the present invention involves a head assembly for a material testing machine. The head assembly comprises a load assembly. The load assembly comprises a load sensor that is connected to an indenter. The indenter and the load sensor are connected along a sensing axis such that loads applied to the indenter along the sensing axis can be detected by the load sensor. A non-contact sensor is secured to the load assembly. The head assembly is moveable along the sensing axis.

Certain features, aspects and advantages of the present invention also relate to a method of measuring a penetration depth of an indenter. The method comprises positioning a non-contact sensor generally adjacent to the indenter, lowering the indenter toward a sample surface, setting a reference point for the non-contact sensor, further lowering the indenter and measuring a load applied to the indenter and measuring a vertical movement from the reference location during application of the load without contacting the sample surface.

BRIEF DESCRIPTION OF THE DRAWINGS

These and other features, aspects and advantages of the present invention will now be described with reference to the drawings of a preferred embodiment, which embodiment is intended to illustrate and not to limit the invention, and in which figures.

DETAILED DESCRIPTION OF THE PREFERRED EMBODIMENT

Figure 1:
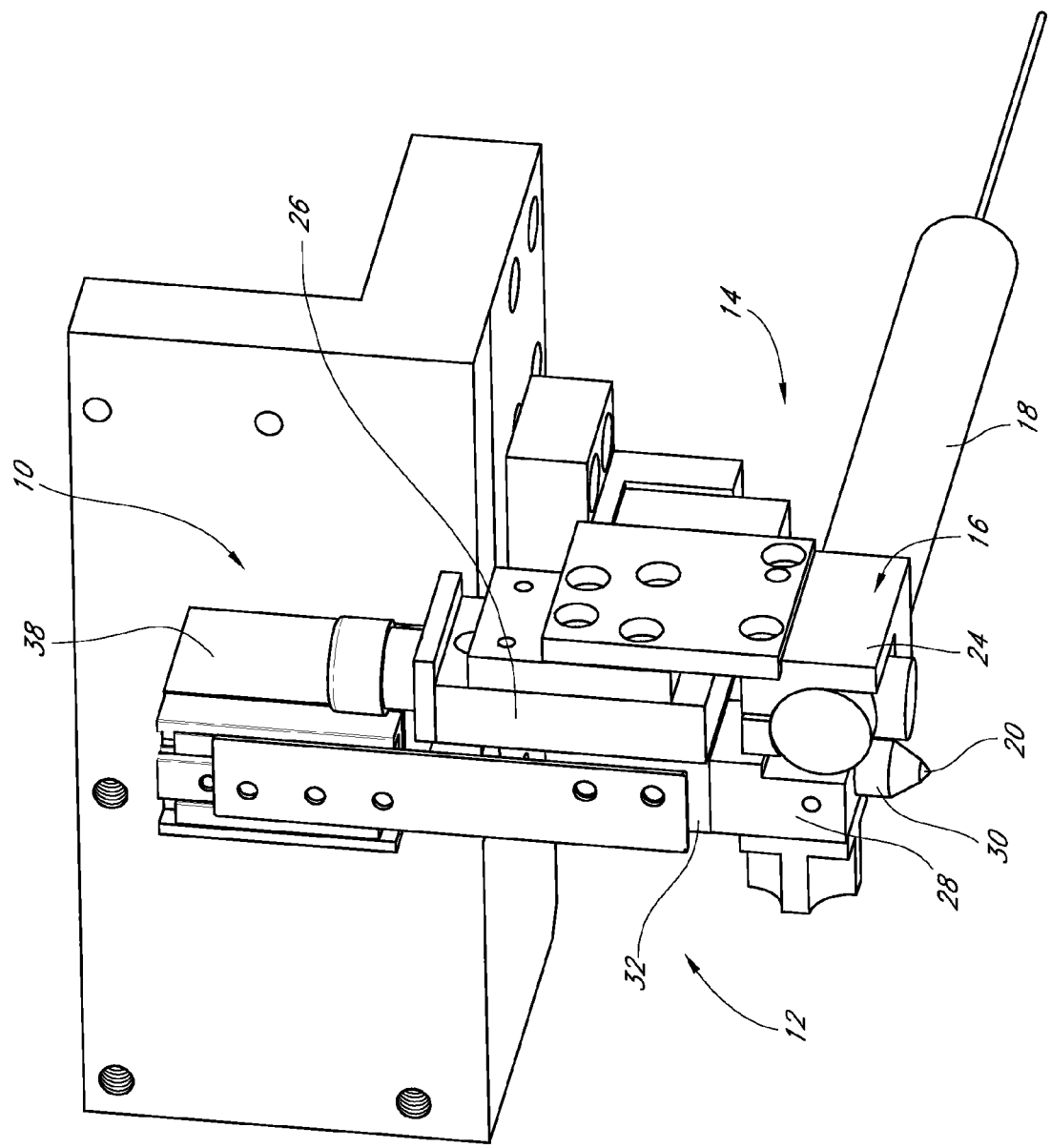
FIG. 1 is a perspective view of a non-contact depth sensor assembly attached to a load cell/indenter assembly that is arranged and configured in accordance with certain features, aspects and advantages of the present invention.

With reference initially to FIG. 1, one embodiment of an assembly that is arranged and configured in accordance with certain features, aspects and advantages of the present invention is shown therein. As shown, a head assembly 10 generally comprises a load cell/indenter assembly 12 and a non-contact depth sensor assembly 14. The non-contact depth sensor assembly 14 preferably comprises a non-contact depth measuring module 16 that mounts directly on the load cell/indenter assembly 12 such that the head assembly 10 becomes a full measuring head that can be used in a scratch, hardness and/or wear tester. The non-contact depth sensor assembly 14 also comprises a non-contact sensor 18.

The non-contact sensor 18 can be any suitable non-contact sensor. In one embodiment, the non-contact sensor 18 can be based on a white light axial chromatism technique. Axial chromatism works on a very wide range of materials, including, among other materials, polymers, plastics, glasses, metals, and ceramics. Axial chromatism advantageously allows signals to return from high angular surfaces, which allows measurements on curved surfaces or rougher materials, for example.

The non-contact sensor 18 can be an optical sensor in some configurations. One optical sensor, which works using axial chromatism, can have a full range of approximately 300 microns and can have a radius of approximately 12 mm. The optical sensor preferably is chosen primarily to reduce the weight of the assembly 14 and to minimize the distance between an indenter tip 20 and a spot of light that emanates from the non-contact sensor 18. Preferably, the optical sensor can be used at an approximately 90 degree angle relative to the body or housing of the optical sensor, which facilitates mounting of the optical sensor (i.e., decreases the vertical dimension of the head assembly) and which reduces the weight of the assembly 14. In other words, the housing or body of the optical sensor preferably is generally normal to the direction of movement of the load cell/indenter assembly 12. The sensor preferably has also a range of resolution that makes it a good choice for a micro range load down to 50 mN. The manufacturer of the sensor 18 (e.g., pen) and an associated sensor controller (not shown) can be STIL SA.

Other types of sensors and sensor arrangements also can be used, such as, for example, laser interferometers, laser triangulation, infrared sensors, PSD, capacitive and inductive sensors, and the like. In some embodiments, an endoscopy lens can be used to bring the light closer to the point of measurement. Preferably, a distance between the indenter tip 20 and the spot of light from the sensor 18 is minimized to decrease the effect of surface movements at high loads where it might be more difficult to clamp effectively the sample and to reduce the likelihood of micron level surface movement.

With reference again to FIG. 1, the non-contact sensor 18 preferably is supported by a sensor holder 24. The sensor holder 24 can be connected to a miniature micrometer table 26 with a plate 27, for example. In some configurations, the sensor holder 24 can be directly connected to the table 26. Advantageously, the table 26 allows at least vertical adjustment of the sensor 18 relative to the indenter assembly 12. In some configurations, the table 26 allows at least vertical adjustment of the sensor 18 relative to an indenter holder 28, which supports the indenter 30. In some configurations, the table 26 allows at least vertical adjustment of the sensor 18 relative to a load cell 32. In some configurations, the table 26 allows at least vertical adjustment of the sensor 18 relative to the load cell 32 and the indenter holder 28, which supports the indenter 30. The table 26 can allow movement of at least approximately 4 mm, which is sufficient to adjust for various surface conditions, such as surface curvature, surface profiles, or height variations, for example but without limitation. Desirably, the table 26 minimizes the weight added to the system but while being sufficiently sturdy to support the weight of the non-contact sensor 18.

The non-contact sensor 18 preferably is positioned such that its working range substantially encompasses the tip 20 of the indenter 30. In other words, the proximal and distal ends of the functional range of the sensor 18 preferably are respectively positioned on each side of the tip 20 of the indenter 30. In the illustrated configuration, the position of the sensor 18 can be adjusted in two planes relative to the sensor holder 24 while the sensor 18 can be adjusted in three directions relative to the indenter 30. More preferably, the sensor 18 can be adjusted axially or radially relative to the sensor holder 24 while the sensor 18 can be adjusted axially, radially or vertically relative to the indenter 30. Other configurations can be used. In some configurations, the sensor 18 is not adjustable relative to the indenter 30.

The load cell 32 preferably has sufficient surface area on which to secure the table 26, which supports the non-contact sensor 18. While the illustrated configuration uses the load cell 32, other types of load sensors also can be used. One suitable load cell 32, for example but without limitation, is a fatigue rated minibeam load cell identified as model MBI 50N from Interface, Inc. of Scottsdale, Ariz.

In some embodiments, the load cell 32 can be modified to generally minimize the distance between the tip 20 of the indenter 30 and the location on the sample surface that is measured by the non-contact sensor 18. Because of local deformation caused by the test, it is preferable to provide a separation of at least approximately 1 mm between the point of physical measurement with the indenter 30 and the non-contact measurement with the sensor 18. In some configurations, the separation is between approximately 4 mm and 6 mm. It is believe that, as long as the sample being tested is well-secured, the separation should not cause significant deviation in data collected.

A frictionless bearing slide 36 can be preferably used to further secure the load cell 32 and allow generally free movement only in the direction of measurement. The full head assembly 10 preferably is moved down using a servo motorized table 38 with high gear ratio (400,000 steps). In some configurations, other motors (e.g., stepper motors), electromagnet systems or lead screw assemblies can be used to move the module 16 in a controlled manner.

Figure 2:
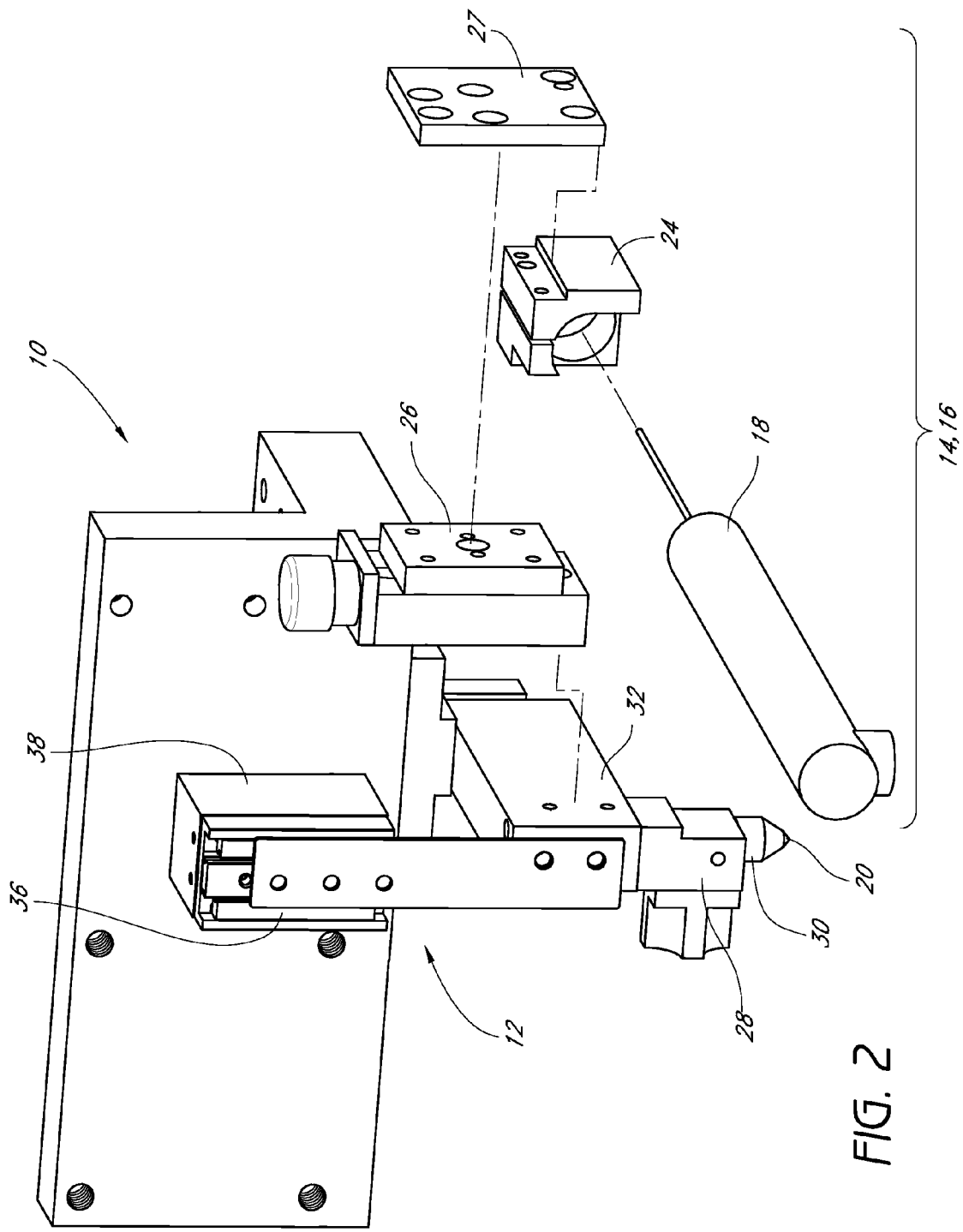
FIG. 2 is a partially exploded view of the assembly of FIG. 1
Figure 3:
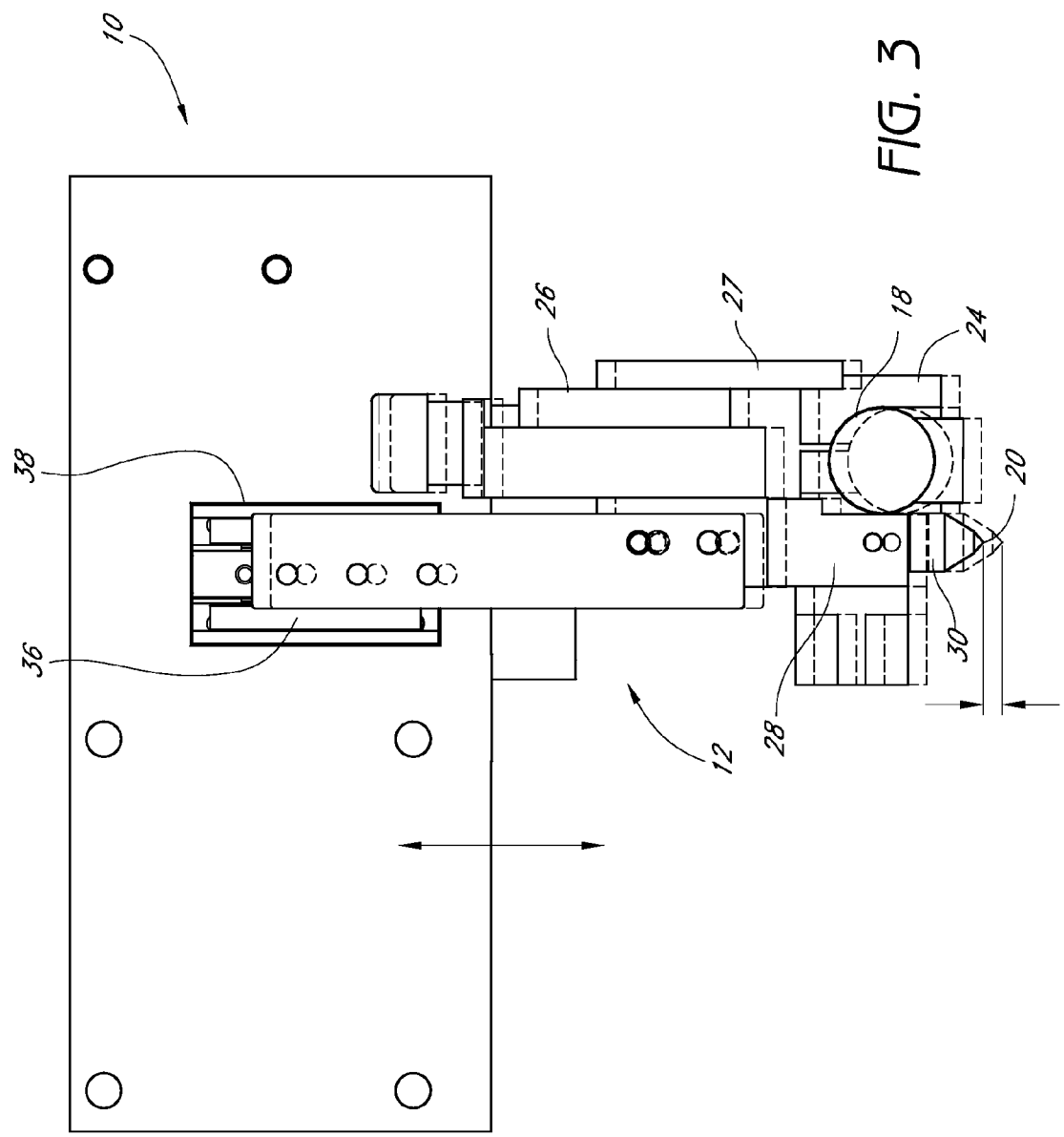
FIG. 3 shows a change in position of the assembly of FIG. 1 when the indenter is penetrating the sample and the non-contact sensor is measuring the position of the sample surface.

With a suitable construction, such as that shown in FIG. 1, while the full assembly 10 is moved downward, as shown in FIG. 2, the penetration depth of the indenter 30 can be recorded from a signal originating from the non-contact sensor 18 while the load can be concurrently measured by the signal originating from the load cell 32. While not shown, software can acquire the data from the two sensors 18, 32 and can plot the results of the test according to the type of test being conducted.

For example, when hardness testing is conducted, as the tip 20 of the indenter 30 touches the surface of the sample, the load cell 32 detects the contact load and the non-contact depth sensor 18 records the initial position corresponding to the surface of the sample. As the load cell assembly 12 is brought down further, the force applied by the indenter 30 to the sample surface increases and the indenter 30 gradually penetrates the sample surface as the load registered by the load cell 32 increases. The variation in depth detected by the non-contact sensor 18 is recorded at the same time. The acquisition of the position and load data in real-time allows the plotting of instrumented indentation depth versus load curves, for example.

In some embodiments, the tip 20 of the indenter 30 is driven into a sample by applying an increasing load to a preset value. The load is then gradually decreased until partial, or complete, relaxation of the sample has occurred. The load and the displacement can be recorded periodically or continuously through the process to produce a load and displacement curve. Adding a pause at the maximum or preset load can allow the creep properties of the sample to be studied.

During scratch or wear testing of the sample, as the tip 20 of the indenter 30 touches the surface of the sample, the load cell 32 detects the contact load and the non-contact depth sensor 18 records the initial position corresponding to the surface of the sample. Concurrently, in some embodiments, the sample moves laterally with respect to the indenter 30 at any chosen speed or speeds and in any chosen direction or directions. The movement can vary depending on the test. For example, linear movement often is used for scratch or wear testing and circular movement often is used for wear testing. As the head assembly 10 is brought down further and the sample is moving, the force applied through the indenter 30 to the surface of the sample increases and the indenter 30 penetrates the sample as the load registered by the load cell 32 increases. The variation in depth obtained by the non-contact sensor 18 is recorded at the same time. The acquisition of depth versus displacement or load during scratch or wear testing allows measuring of failure points and wearing rates, for example.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A head assembly for a material testing machine, the head assembly comprising a load assembly, the load assembly comprising a load sensor that is connected to an indenter, the indenter and the load sensor being connected along a sensing axis such that loads applied to the indenter along the sensing axis can be detected by the load sensor, and a non-contact sensor for measuring displacement of the non-contact sensor along the sensing axis with direct reference to a surface of a test sample, the non-contact sensor being secured to the load assembly, and the head assembly being moveable along the sensing axis, wherein the non-contact sensor can be adjusted along a first axis that is substantially parallel to the sensing axis, along a second axis that is substantially normal to the first axis and rotationally relative to the second axis.

2. The head assembly of claim 1, wherein an intervening structure connects the non-contact sensor to the assembly.

3. The head assembly of claim 2, wherein the intervening structure comprises an adjustable table.

4. The head assembly of claim 3, wherein the adjustable table allows movement of the non-contact sensor relative to the indenter along an axis that is substantially parallel to the sensing axis.

5. The head assembly of claim 2, wherein the intervening structure comprises a sensor holder.

6. The head assembly of claim 5, wherein the sensor holder secures the noncontact sensor while allowing movement of the non-contact sensor relative to the indenter along an axis that is substantially perpendicular to an axis that is substantially parallel to the sensing axis.

7. The head assembly of claim 5, wherein the non-contact sensor is adjustable relative to the sensor holder.

8. The head assembly of claim 7, wherein the non-contact sensor is rotationally adjustable relative to the sensor holder.

9. The head assembly of claim 7, wherein the non-contact sensor is axially adjustable relative to the sensor holder.

10. The head assembly of claim 5, wherein the non-contact sensor comprises a body and the body extends in a direction that is generally normal to an axis that is generally perpendicular to the sensing axis.

11. The head assembly of claim 5, wherein the intervening structure further comprises an adjustable table and the sensor holder connects the non-contact sensor to the adjustable table.

12. The head assembly of claim 11, wherein the adjustable table allows movement of the non-contact sensor relative to the indenter along an axis that is substantially parallel to the sensing axis.

13. The head assembly of claim 1, wherein the non-contact sensor is selected from the group consisting of: white light sensors, optical sensors, laser interferometers, laser triangulation sensors, infrared sensors, position sensitive detector sensors, capacitive sensors and inductive sensors.

14. The head assembly of claim 13, wherein the non-contact sensor comprises an optical sensor.

15. The head assembly of claim 1, wherein the load sensor comprises a load cell.

16. A head assembly for a material testing machine, the head assembly comprising a load assembly, the load assembly comprising a load sensor that is connected to an indenter, the indenter and the load sensor being connected along a sensing axis such that loads applied to the indenter along the sensing axis can be detected by the load sensor, and a non-contact sensor being secured to the load assembly, and the head assembly being moveable along the sensing axis, wherein the non-contact sensor comprises a white light sensor.

17. The head assembly of claim 16, wherein the non-contact sensor comprises an axial chromatic white light sensor.

18. A head assembly for a material testing machine, the head assembly comprising a load assembly, the load assembly comprising a load sensor that is connected to an indenter, the indenter and the load sensor being connected along a sensing axis such that loads applied to the indenter along the sensing axis can be detected by the load sensor, and a non-contact sensor being secured to the load assembly, and the head assembly being moveable along the sensing axis, wherein the load sensor comprises a load cell, wherein the load cell comprises a fatigue rated minibeam load cell.

19. The head assembly of claim 18, wherein the non-contact sensor is selected from the group consisting of: white light sensors, optical sensors, laser interferometers, laser triangulation sensors, infrared sensors, position sensitive detector sensors, capacitive sensors and inductive sensors.

20. The head assembly of claim 18, wherein the non-contact sensor comprises an axial chromatic white light sensor.

* * * * *